＝

US008846640B2

(12) United States Patent
D'este et al.

(10) Patent No.: US 8,846,640 B2
(45) Date of Patent: Sep. 30, 2014

(54) VISCOELASTIC GELS AS NOVEL FILLERS

(75) Inventors: Matteo D'este, Abano Terme (IT); Davide Renier, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 13/392,479

(22) PCT Filed: Aug. 25, 2010

(86) PCT No.: PCT/EP2010/005161
§ 371 (c)(1),
(2), (4) Date: Apr. 9, 2012

(87) PCT Pub. No.: WO2011/023355
PCT Pub. Date: Mar. 3, 2011

(65) Prior Publication Data
US 2012/0190644 A1     Jul. 26, 2012

(30) Foreign Application Priority Data
Aug. 27, 2009    (IT) .............................. PD2009A0246

(51) Int. Cl.
| | | |
|---|---|---|
| *A61L 27/26* | (2006.01) | |
| *A61L 27/54* | (2006.01) | |
| *C08L 5/08* | (2006.01) | |
| *C08J 3/14* | (2006.01) | |
| *C08B 37/08* | (2006.01) | |
| *C08J 3/075* | (2006.01) | |
| *C08J 3/24* | (2006.01) | |
| *C08B 37/00* | (2006.01) | |
| *C08J 3/00* | (2006.01) | |

(52) U.S. Cl.
CPC .. *A61L 27/54* (2013.01); *C08J 3/14* (2013.01); *C08L 5/08* (2013.01); *C08B 37/0072* (2013.01); *C08J 3/075* (2013.01); *A61L 2300/402* (2013.01); *C08J 3/24* (2013.01); *C08L 2205/02* (2013.01); *C08B 37/0003* (2013.01); *C08J 2305/08* (2013.01); *A61L 27/26* (2013.01); *A61L 2430/34* (2013.01); *A61L 2300/602* (2013.01); *C08J 3/005* (2013.01)
USPC ............................................................ 514/54

(58) Field of Classification Search
CPC ............ A61L 27/26; A61L 27/54; C08L 5/08
USPC .................................................................. 514/54
See application file for complete search history.

(56) References Cited

U.S. PATENT DOCUMENTS

| | | | | |
|---|---|---|---|---|
| 5,676,964 | A | * | 10/1997 | Della Valle et al. ........... 424/423 |
| 7,884,087 | B1 | * | 2/2011 | Bellini et al. ................... 514/54 |
| 8,357,795 | B2 | * | 1/2013 | Lebreton ...................... 536/124 |
| 2008/0069884 | A1 | * | 3/2008 | Schiavinato et al. ......... 424/488 |
| 2010/0316683 | A1 | * | 12/2010 | Piron et al. .................... 424/401 |

FOREIGN PATENT DOCUMENTS

| | | | | |
|---|---|---|---|---|
| EP | 0193510 | A1 | | 9/1986 |
| EP | 0341745 | A1 | | 11/1989 |
| FR | WO2008/068297 | * | 6/2008 | ................... 424/401 |
| WO | WO-97/49412 | A1 | | 12/1997 |
| WO | WO-99/24070 | A2 | | 5/1999 |
| WO | WO-2005/112888 | A2 | | 12/2005 |
| WO | WO-2008/068297 | A1 | | 6/2008 |
| WO | WO-2009/073437 | A1 | | 6/2009 |

* cited by examiner

*Primary Examiner* — Brandon Fetterolf
*Assistant Examiner* — Yih-Horng Shiao
(74) *Attorney, Agent, or Firm* — Birch, Stewart, Kolasch & Birch, LLP

(57) ABSTRACT

Biomaterials obtainable by mixing
    the autocrosslinked derivative of hyaluronic acid (ACP) with
    the derivative (HBC) of hyaluronic acid crosslinked with 1,4-butanediol diglycidyl ether (BDDE) in the weight ratio of between 10:90 and 90:10 as novel fillers.

16 Claims, 1 Drawing Sheet

VISCOELASTIC GELS AS NOVEL FILLERS

CROSS-REFERENCE TO RELATED APPLICATION

This application is the National Phase Under 35 U.S.C. §371 of PCT International Application No. PCT/EP2010/005161 which has an International filing date of Aug. 25, 2010, which claims priority to Italian Patent Application No. PD2009A 000246 filed on Aug. 27, 2009. The entire contents of all applications listed above are hereby incorporated by reference.

SUBJECT OF THE INVENTION

Viscoelastic gels as novel filters

FIELD OF INVENTION

Hyaluronic acid (HA) is a heteropolysaccharide consisting of alternating residues of D-glucuronic acid and N-acetyl-D-glucosamine.

HA is a straight-chain polymer with a molecular weight ranging between 50,000 and $13 \times 10^6$ Da, depending on the source from which it is obtained and the preparation methods used.

HA is present in nature in pericellular gels, in the ground substance of the connective tissue of vertebrates (of which it is one of the main components), in the vitreous humour and in the umbilical cord.

HA plays an important part in the biological organism as a structural and mechanical support for the tissues, and as an active component in the cell physiology of tissues such as skin, tendons, muscles and cartilage.

It is one of the main molecules in cartilage matrix, and also represents the main non-protein constituent of synovial fluid. As it is a strongly hydrophilic viscoelastic molecule, it gives the synovial fluid lubricant properties; HA has therefore been used in osteoarthritis for over 30 years, mainly to treat the associated pain.

HA also plays a crucial role in the tissue repair process from the structural standpoint (in the organisation of the extracellular matrix and regulation of its hydration), and as stimulating/regulating substance of a wide range of physiological processes wherein said polysaccharide acts directly and/or indirectly (clot formation, phagocyte activity, fibroblast proliferation, neovascularisation, re-epithelialisation, etc.) (Weigel P. et al., *J Theoretical Biol*, 1986:219-234; Abatangelo G. et al., *J Surg Res*, 1983, 35:410-416; Goa K. et al., *Drugs*, 1994, 47:536-566). As these properties have long been recognised, HA is also used to prepare dressings for the care of wounds, ulcers and skin lesions of various origins.

Hyaluronic acid is also used as a filler for wrinkles, furrows and small depressed areas of the face, and to increase the volume of the lips and cheeks, because it is immunologically inert, non-toxic, biodegradable and bioresorbable.

Treatment based on hyaluronic acid is indicated for the correction of:
lip volume and contours
furrows (e.g. nasolabial folds)
remodelling of facial contours (e.g. cheeks and chin)
wrinkles (e.g. glabellar lines and oral commissures)
periorbital wrinkles
fibrous post-acne scars
fibrous post-traumatic scars
soft tissue blemishes
rhinoplasty scars.

Hyaluronic acid is not a permanent filler. This means that once injected, the product is gradually metabolised and resorbed by the body in times varying according to the area treated and the type of preparation used. The effect of filling and increased volume (or attenuation of wrinkles) is immediate, and only lasts a few weeks. The main products present on the market can be classified under the following categories, based on their different resorption times:
rapid-resorption fillers (2-3 months),
medium-term resorption fillers (5-6 months),
slow-resorption fillers (1 year) such as Restylane Sub Q (QMed, EP0839159).

In the dermis, HA performs hydrating functions due to its high capacity to bind water, and structural functions as "scaffolding" because, by binding to other substances, it forms macromolecular complexes which render the skin compact.

The action mechanism therefore consists of immediate volumetric filling due to the viscoelastic properties of the product, and new collagen synthesis due to stimulation of the cutaneous fibroblasts.

However, HA is a natural polysaccharide which is rapidly broken down by the hyaluronidase enzymes present in connective tissue; in order to obtain fillers whose effect lasts for several months, HA is therefore subjected to crosslinking processes which improve its viscoelastic properties and increase its residence time. The fillers thus formed are crosslinked, for example, through BDDE (1,4-butanediol diglycidyl ether, Restylane®, BELOTERO® and Regenyal Idea) or DVS (divinyl sulphone, Hylaform®), which create bridges between the polymer molecules. However, increasing the degree of crosslinking progressively denatures the HA to the extent of profoundly modifying its chemical, physical and biological properties. Excessively crosslinked HA matrices present as particulate solids which are no longer recognised by the cells (and especially by the immune system) as HA; the polysaccharide is therefore perceived as a foreign body, which triggers inflammatory reactions with the formation of fibrotic capsules around it. Moreover, excessively crosslinked HA is unable to stimulate the dermal/cutaneous tissue regeneration induced, as known from well-established scientific results, by HA fragments (especially those with a low molecular weight) which have the effect of stimulating collagen synthesis by the cutaneous fibroblasts.

Fillers are also classified as resorbable or permanent. The resorbable type are the most biocompatible; they consist of hyaluronic acid or collagen, either modified or present in their native form, and are consequently resorbed within a year at most. The permanent type consist of synthetic polymers such as polyacrylamides, particular crosslinked molecules which form a stable gel when combined with water. The permanent type always remain in situ and are very useful for filling the lips, but their use is not recommended because acute inflammations are increasingly often caused by their cutaneous insertion, leading to the formation of fibrotic capsules around the filler, which is perceived as a foreign body and therefore toxic.

The applicant has perfected a novel type of biomaterial as new filler and/or as new product for body shaping, formed by mixing two HA derivatives crosslinked in different but complementary ways, to obtain a skin/tissue substitute which allows immediate hydration (and consequently immediate filling) of the treated skin/tissue, while maintaining very long in vivo breakdown times to eliminate the need for repeated injections, thus reducing the side effects.

The novel biomaterials to which the present invention relates present particular characteristics of biocompatibility identical to those of hyaluronic acid as such, but their biodegradability is different; when implanted in vivo, their residence time is much longer than that of unmodified HA, thus allowing immediate regeneration/reconstruction of dermal/cutaneous tissue which has lost its original compactness.

DETAILED DESCRIPTION OF THE INVENTION

Figure 1:
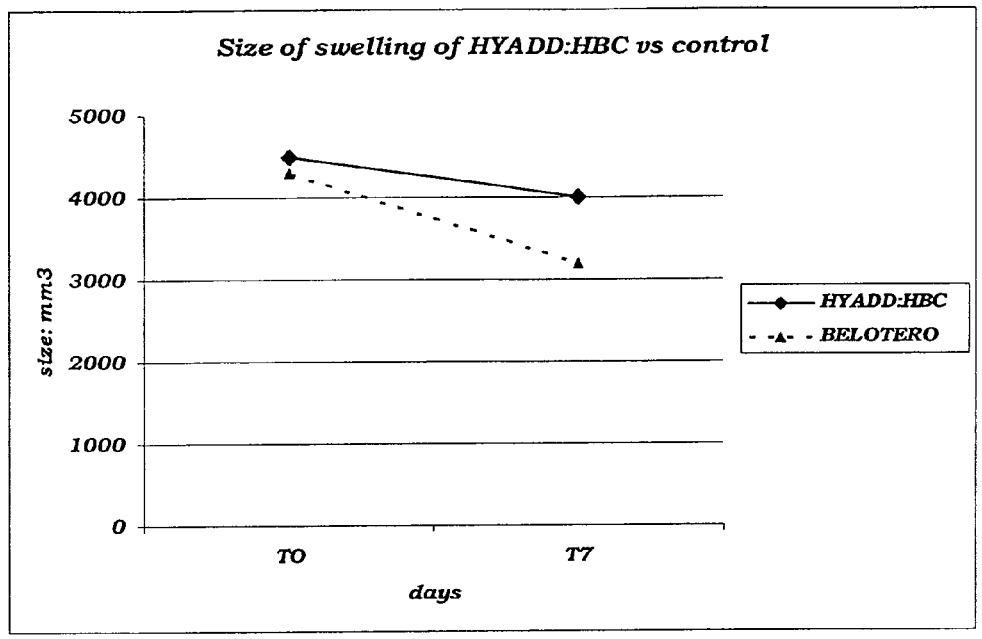
FIG. 1 graphs the results of a test on the cutaneous filling and tolerability of HYADD:HBC gel in the intradermal rabbit administration model.

The applicant has perfected a novel type of biomaterial as new filler and/or as new product for body shaping based on mixing two HA derivatives with different but complementary characteristics to obtain a novel product for injection in the treatment of skin blemishes, in dermatology, in dermocosmetology and/or in aesthetic surgery, which produces:
1. immediate dermal/cutaneous hydration
2. immediate filling of the treated tissue
3. very long breakdown times in vivo
4. reduced side effects.

The novel biomaterials consist of:
autocrosslinked hyaluronic acid (ACP) or HA hexadecylamide (HYADD), mixed with
hyaluronic acid crosslinked with BDDE (HBC).

The ACP used in the present invention, prepared as described in EP 0341745, possesses a mean degree of crosslinking of between 4 and 5% and is preferably prepared using HA with a mean molecular weight (MW) of 200 KDa. When hydrated it presents as an autocrosslinked gel with no molecules foreign to the native polysaccharide, because it arises from the ester bond between the carboxyl and hydroxyl groups of the same polysaccharide chain and/or adjacent chains. It is therefore devoid of immunotoxicity, as biocompatible as native HA, highly moisturising, and easily degradable by hyaluronidases, releasing molecules with a low molecular weight able to stimulate collagen synthesis to improve the tone and elasticity of the cutaneous tissue.

HA hexadecylamide (HYADD) is prepared as described in EP 1095064 and EP1853279, preferably using HA with a mean molecular weight (MW) of 500-730 KDa, with a mean degree of final amidation/substitution of between 1 and 3% in moles.

ACP and HYADD are the HA derivatives responsible for the immediate hydration (leading to instant dermal filling) elicited by the intradermal injection of the filler to which the present invention relates.

HA crosslinked with BDDE (a molecule containing epoxy groups for the formation of ethers on the primary hydroxyls of HA) contains the crosslinking molecule, and is therefore more resistant to enzymatic degradation as it possesses ether bonds which stabilise the polysaccharide, giving the product obtained a long residence time.

Mixing of the two species of crosslinked HA leads to the formation of a novel biomaterial which has biocompatibility characteristics identical to those of native hyaluronic acid, but a different biodegradability so that, when implanted in vivo, its residence time is much longer than that of unmodified HA, thus allowing the regeneration/reconstruction of dermal tissue which has lost its original compactness. The Applicant has also demonstrated that their association quite unexpectedly leads to an in vivo breakdown time much longer than that of the commercial reference fillers formed by the same type of HA crosslinked with BDDE, with a consequent increase in residence time. Finally, the Applicant claims the use of the novel biomaterials as fillers and/or as new products for body shaping in the treatment of skin blemishes, in dermatology, in dermocosmetology and/or in aesthetic surgery.

The chemically heterogeneous nature of the novel biomaterial allows the properties of the end product to be modulated by suitably varying the weight ratio between the constituents. The two HAs can be mixed in the ACP (or HYADD):HBC ratio of 10:90 to 90:10: the weight ratio will be selected on the basis of the desired final viscosity, which will depend on the site treated. If areas requiring implantation of large amounts of biomaterial are to be treated, as in the case of filling of the breasts, buttocks, cheeks or chin, or deep expression wrinkles, the biomaterial used will preferably present good compactness, and therefore a viscosity suitable to obtain a gel with an excellent consistency and a low biodegradability rate; in this case the ACP (or HYADD):HBC mixture will be between 10:90 and 50:50, and preferably 25:75, because the product obtained by increasing the weight fraction of HBC is more suitable to perform a longer-lasting volume-enhancing effect. However, if lip furrows or fine forehead wrinkles are to be treated, the ACP (or HYADD):HBC ratio will preferably be between 90:10 and 50:50, as a higher fraction of ACP in the filler produces a material more suitable for biorevitalization of the skin and correction of fine lines, minor expression wrinkles and the like. Moreover, the needle must have a very high gauge; the gel must therefore be easily extrudable and less viscous than the one described above. The rheological properties of the product are consequently adjustable on the basis of the selected ACP:HBC ratio.

ACP (or HYADD)/HBC composition being equal, the properties of the biomaterial can also be suitably modulated by means of a targeted selection of the vehicle in which it is prepared: for example, an ACP:HBC 50:50 weight mixture dispersed in saline solution (0.9% NaCl) will be more viscous than if it is dispersed in phosphate buffer at pH=6.95; consequently, for this specific mixture, saline solution is a more suitable medium for the formulation of products with a limited dispersion rate in situ. Materials consisting of a prevalence of HBC exhibit the opposite profile. The viscoelastic properties of the material consequently affect the performance of the product.

The present invention also relates to the two biomaterials preparation processes described above: process A and process B.

The novel processes A and B are divided into two steps:
1. process for the production of the HBC derivative, and
2. process for mixing it with the ACP or HYADD derivative.

The two steps lead to the production of products with a very high degree of purity. With the methods normally used for the production of HA crosslinked with BDDE, the purifications are performed by washing the mass of gel obtained, or by dialysis. In both cases, optimum purification efficiency may not be achieved due to the nature of the gel matrix which, in view of its tendency to swell, incorporates large amounts of solvent. These gels have low mobility and transport capacity, and tend to precipitate as gelatinous gums. The precipitate thus obtained, isolated as a solid, has different solubility and rheology properties when rehydrated, especially swelling capacity, elasticity and homogeneity (essential characteristics for a filler), from the gel before purification.

However, the method hereinafter described by the Applicant as process A precipitates the product in the form of a finely divided powder, which is consequently easily washable. Moreover, the careful choice of reaction conditions produces, after isolation by precipitation and washing, a product with gel reconstruction capacity by means of rehydration and sterilisation which gives rise to a biomaterial having reproducible, well standardised characteristics of elasticity and homogeneity.

Process B does not include the step of precipitation of the HBC product as a powder; the purification and homogenisation of the gel (obtained after mixing HBC with ACP or HYADD) is effected at the crushing step, which involves passing it through a filter with a particulate matter retention coefficient of between 25 and 150 µm. This step purifies the final gel and makes it perfectly homogenous.

The HA used in the present invention to prepare the derivatives described above (HBC, ACP and HYADD) can derive from any source, such as extraction from cockscombs or fermentation, and have a mean molecular weight of between 400 and $3 \times 10^6$ Da, preferably between $1 \times 10^5$ Da and $1 \times 10^6$ Da, and even more preferably between 200,000 and $1 \times 10^6$ Da.

Novel manufacturing process A comprises the following steps:

Synthesis of Crosslinked HBC

1. Dissolution in alkaline solution (preferably 0.15M-0.35M NaOH) of diepoxide BDDE in a stoichiometric ratio of between 2.5 and 25% in moles, preferably between 5 and 15% in moles (depending on the intended use of the product; the higher the percentage of BDDE, the longer the residence time) of the repetitive units of hyaluronic acid, followed by 2. dispersion of HA in the solution referred to in the preceding paragraph, at room temperature. The HA concentration must be between 80 and 300 mg/ml, and the homogenisation time between 30 and 300 minutes.

3. Triggering of the reaction by heat activation, said solution being heated at a temperature of between 35 and 55° C. for between 2 and 36 hours.

4. Extrusion of the mass obtained through a metal sieve, to reduce it to particles with a size of approx. 600 µm.

5. Hydration of gel by diluting it with water by a factor of 3 to 25, for a time of between 4 and 48 hours at a temperature of 4 to 24° C.

6. Correction of pH to neutral with an aqueous HCl solution having a concentration of 0.5 to 5 moles/l, preferably 1 to 2 moles/l.

7. Addition of 2.5 volumes of water-soluble organic solvent such as ethanol, methanol, isopropanol, n-propanol, dioxane, acetonitrile, acetone and/or mixtures thereof (preferably ethanol and acetone), until the product is obtained in the form of a precipitated powder.

8. Washing with organic solvents such as ethanol, methanol, isopropanol, n-propanol, dioxane, acetonitrile, acetone and/or mixtures thereof (preferably ethanol and acetone), containing a water fraction of under 35%.

9. Drying under vacuum at a temperature of between 30 and 45° C. for between 2 and 7 days, and in any event until elimination of the residual solvents under 400 ppm, to obtain a white HBC powder.

Mixing of ACP (or HYADD) with HBC

10. Mixing of the HBC powder with ACP (or HYADD) powder in an ACP:HBC ratio of between 10:90 and 90:10 (depending on the use chosen, as previously described).

11. Hydration with saline solution or phosphate buffer, preferably saline solution (which may contain further excipients such as lidocaine), leading to a total HA concentration of between 12 and 27 mg/ml, preferably between 20 and 25 mg/ml, at a temperature of between 0 and 26° C.

12. Extrusion through a sieve with a mesh of between 50 and 500 µm, preferably between 100 and 250 µm. Said filtration is performed at room temperature, or at a temperature of between 25 and 65° C., preferably between 40 and 60° C.

13. Filling of syringes, preferably made of glass or polymer material, with the product obtained.

14. Heat sterilisation with saturated steam at a temperature of between 120 and 124° C. (preferably 121.5±1° C.) for at least 10 min.

Novel manufacturing process B comprises the following steps:

Synthesis of Crosslinked HBC

1. Dissolution in alkaline solution (preferably 0.15M-0.35M NaOH) of diepoxide BDDE in a stoichiometric ratio of 2.5 to 25% in moles, preferably between 5 and 15% in moles (depending on the intended use of the product) of the repetitive units of hyaluronic acid, followed by.

2. dispersion of HA in the solution referred to in the preceding paragraph, at room temperature. The HA concentration must be between 80 and 300 mg/ml, and the homogenisation time between 30 and 300 minutes.

3. Triggering of the reaction by heat activation, said solution being heated at a temperature of between 35 and 55° C. for between 2 and 36 hours.

4. Correction of pH to neutral with an aqueous HCl solution having a concentration of 0.05 to 1 moles/l, preferably 0.1 moles/l.

5. Hydration of gel by diluting it with water by a factor of 3 to 20 for a time of between 4 and 48 hours at a temperature of 4 to 24° C. This solution may contain further excipients, such as NaCl, phosphoric acid sodium or potassium salts, and lidocaine, preferably in the form of hydrochloride salt. Sodium salts (chloride or phosphate) have the function of maintaining the appropriate osmolarity of the product, and maintaining the pH at a value compatible with the tissues. In a preferred embodiment of the invention, NaCl is added in an amount such that the final solution contains a concentration of between 0.8 and 1.0% thereof, preferably 0.9%; the lidocaine hydrochloride, if present, is added in an amount such that the final formulation contains an amount of between 2.2 and 3.2 mg/ml thereof, preferably 2.7 mg/ml.

Mixing of ACP (or HYADD) with HBC

6. Mixing of the HBC gel with ACP (or HYADD) powder in the ACP (or HYADD):HBC ratio of between 10:90 and 90:10 (in weight of the active ingredient) depending on the use chosen for the novel filler, as previously described. Alternatively, the ACP or HYADD can be mixed with HBC starting with both components in gel form, using a suitable stirring system (preferably with an orbital blade) for a time of between 30 minutes and 24 hours at a temperature of between 0 and 26° C.

7. Crushing and homogenisation by passing through a filter with a particulate matter retention coefficient of between 25 and 150 µm, preferably between 40 and 110 µm. If the viscosity is excessive, the operation can be performed hot, at a temperature of between 25 and 65° C.

8. Filling of syringes, made of glass or polymer material, with the product obtained.

9. Sterilisation by heat from saturated steam at a temperature of between 120 and 124° C. (preferably 121.5±1° C.) for at least 10 min.

Some examples of preparation of the novel filler according to the invention are described below, by way of example and not of limitation.

Example 1

Synthesis of HBC 500 (HA 500-730 kDa)

Process A 0.075 moles of HA with a molecular weight of 500-730 kDa, produced by fermentation, are dispersed in 215 ml of an 0.25M NaOH solution containing 1.41 ml of BDDE. The mixture is then heated to 42° C. and reacted for 3 hours. The mixture is then hydrated for 24 h with 300 ml of a solution containing a stoichiometric amount of HCl to adjust the pH to neutral. The total volume is made up to 750 ml and precipitated with 2.5 volumes of ethanol to obtain a filterable, decantable precipitate. The mixture is washed with 75% ethanol until exhaustive purification, verified by measuring the specific conductivity of the washing solvents, which should be under 30 μS/cm, and dried under vacuum at 40° C. for 5 days. The HBC 500 product is obtained with a weight yield of 87%.

Example 2

Synthesis of HBC 1000 (HA 1 MDa)

Process A 1.60 g of HA with a mean molecular weight of 1 MDa, produced by fermentation, is dispersed in 20 ml of an 0.25M NaOH solution containing 75 μl of BDDE. The mixture is then heated to 42° C. and reacted for 2 hours. The mixture is then hydrated for 24 h with 20 ml of a solution containing a stoichiometric amount of HCl to adjust the pH to neutral. The total volume is made up to 75 ml and HBC is precipitated with 2.5 volumes of ethanol to obtain a filterable, decantable precipitate. The mixture is washed with 75% ethanol until exhaustive purification, verified by measuring the specific conductivity of the washing solvents, which should be under 30 μS/cm, and dried under vacuum at 40° C. for 5 days. The product HBC 1000 is obtained with a weight yield of 90%.

Example 3

Synthesis of HBC 200 (HA 200 kDa)

Process A 2.55 g of HA with a mean molecular weight of 200 KDa, produced by fermentation, is dispersed in 20 ml of an 0.25M NaOH solution containing 63 μl of BDDE. The mixture is then heated to 42° C. and reacted for 150 minutes. The mixture is then hydrated for 24 h with 20 ml of a solution containing a stoichiometric amount of HCl. The total volume is made up to 75 ml and precipitated with 2.5 volumes of ethanol to obtain a filterable, decantable precipitate. The mixture is washed with 75% ethanol until exhaustive purification, verified by measuring the specific conductivity of the washing solvents, which should be under 30 μS/cm, and dried under vacuum at 40° C. for 5 days. The product HBC 200 is obtained with a weight yield of 85%.

Example 4

Preparation of ACP:HBC 500 Gel, in the Ratio of 50:50

Process A 1.00 g of HBC 500, prepared as described in example 1, is mixed with 1.00 g of HA ACP internal ester. The powder is hydrated with 100 ml of 0.9% weight/volume sterile saline solution at the temperature of 8° C. for 16 hours. The gel obtained is heated to 48° C. and filtered through a metal sieve with a mesh of 0.17 mm, and then distributed between 1 ml glass syringes, which subsequently undergo a sterilisation cycle with saturated steam at the temperature of 121° C. for 10 minutes. A homogenous sterile gel suitable for local administration is obtained.

Example 5

Preparation of ACP:HBC 1000 Gel, in the Ratio of 30:70

Process A 1.40 g of HBC 1000, prepared as described in example 2, is mixed with 0.60 g of HA ACP internal ester. The powder is hydrated with 100 ml of 0.9% w/v sterile saline solution at the temperature of 8° C. for 16 hours. The gel obtained is heated to 48° C. and filtered through a metal sieve with a mesh of 0.17 mm, and then distributed between 1 ml glass syringes, which subsequently undergo a sterilisation cycle with saturated steam at the temperature of 121° C. for 10 minutes. A homogenous sterile gel suitable for local administration is obtained.

Example 6

Preparation of ACP:HBC 500 Gel, in the Ratio of 25:75

Process A 1.875 g of HBC 500, prepared as described in example 1, is mixed with 0.625 g of HA internal ester ACP. The powder is hydrated with 100 ml of 0.9% w/v sterile saline solution at the temperature of 8° C. for 16 hours. The gel obtained is heated to 48° C. and filtered through a metal sieve with a mesh of 0.19 mm, and then distributed between 1 ml glass syringes, which subsequently undergo a sterilisation cycle with saturated steam at the temperature of 121° C. for 12 minutes. A homogenous sterile gel suitable for local administration is obtained.

Example 7

Preparation of ACP:HBC 1000 Gel, in the Ratio of 75:25

Process A 0.50 g of HBC 1000, prepared as described in example 2, is mixed with 1.50 g of HA internal ester ACP. The powder is hydrated with 100 ml of 0.9% w/v sterile saline solution at the temperature of 8° C. for 24 hours. The gel obtained is heated to 42° C. and filtered through a metal sieve with a mesh of 0.17 mm, and then distributed between 2 ml glass syringes, which subsequently undergo a sterilisation cycle with saturated steam at the temperature of 121° C. for 12 minutes. A homogenous sterile gel suitable for local administration is obtained.

Example 8

Preparation of HYADD:HBC 500 Gel, in the Ratio of 60:40

Process A 1.20 g of HBC 500 prepared as described in example 1 is mixed with 0.80 g of HA hexadecylamide (HYADD). The powder is hydrated with 100 ml of 0.9% w/v sterile saline solution at the temperature of 8° C. for 24 hours. The gel obtained is heated to 52° C. and filtered through a metal sieve with a mesh of 0.17 mm, and then distributed between 1 ml glass syringes, which subsequently undergo a sterilisation cycle with saturated steam at the temperature of 121° C. for 11 minutes. A homogenous sterile gel suitable for local administration is obtained.

Example 9

Preparation of HYADD:HBC 500 Gel, in the Ratio of 40:60

Process A 8.0 g of HA sodium salt with a mean molecular weight of 500-730 kDa, produced by fermentation, is dispersed in 40 ml of an 0.25M NaOH solution containing 0.44 ml of BDDE. The mixture is heated at 41.5° C. for 2 hours 40 minutes. It is then hydrated overnight with 100 ml of an 0.1M HCl solution and 200 ml of water. 50 ml of a saturated solution of NaCl is added, and the mixture is left to swell overnight. The next day, 170 ml of acetone and 30 ml of saturated NaCl solution are added, and the mixture is precipitated by slowly adding one liter of ethanol. The precipitate is washed with the same solvent until the NaCl residues have been eliminated, then stove dried at 35° C. under vacuum until the residual solvents have been eliminated. The HBC powder thus obtained is mixed in the ratio of 5:3 with HYADD, prepared as described in patent EP1853279. The mixed powders are hydrated with saline solution, leading to a total concentration of 20 mg/ml (corresponding to 12.5 mg/ml of HBC and 7.5 mg/ml of HYADD4). The product is left to swell overnight at 5° C., and the next day is filtered through a flat membrane with a nominal particulate matter retention rate of 100 µm. 1 ml glass syringes are filled with the product thus obtained and sterilised in a cycle with F0=13 at 121.5° C.

Example 10

Cutaneous Filling and Tolerability of HYADD:HBC Gel in the Intradermal Rabbit Administration Model The purpose of the experiment was to evaluate cutaneous filling, the onset of any macroscopic adverse events, and the tissue response elicited by HYADD:HBC gel (prepared as described in example 9) injected into the intradermal tissue of the rabbit, by comparison with the commercial filler BELOTERO®.

For said evaluation, the gels tested were administered intradermally to male NZW-KBL rabbits weighing 1.8-2.3 kg.

Experiment Design:

The animals were anaesthetised by intravenous administration of ketamine and xylazine. 3 animals were used for each filler tested.

day 0: T0
  Injection of samples (1 ml of hydrogel per sample) after shaving of the rabbits' backs;
  Measurement of the swelling on all rabbits and macroscopic observation for adverse events.
Day 7: T7
  Measurement of swelling volume and macroscopic observation for adverse events.
  The swelling volume was calculated with the formula:

$$(2/3 \times \pi) \times (r1) \times (r2) \times (r3)$$

where: (r1), (r2) and (r3) represent the width, length and height of the swelling respectively, measured with a caliper.

Results:

The novel filler did not cause any inflammatory event in the treated dermis.

The results obtained for the residence time are shown in FIG. 1: the amount of swelling evaluated in the first week's treatment (expressed as $mm^3$) demonstrated that the gel according to the invention is capable of inducing a larger skin swelling volume than the control, which remains high even after 7 days, again to a much greater extent than the commercial filler used as comparator. This finding clearly confirms that the novel fillers immediately produce significant dermal hydration, and this effect is attributable to the presence of the HYADD derivative which, due to its chemical/rheological characteristics, has proved essential to promote immediate cutaneous filling which remains stable over time.

Example 11

Synthesis of HBC 500 (HA 500-730 kDa)

Process B 18.75 g of HA sodium salt with a molecular weight of 500-730 kDa, produced by fermentation, is dispersed in 133 ml of an 0.25M solution of NaOH containing 885 µl of BDDE. The mixture is then heated at 45° C. for 2.5 hours. The mixture is hydrated overnight with 0.62 l of a solution containing a stoichiometric amount of HCl, 2.65 g of NaCl and 2.7 g of lidocaine hydrochloride, under slow stirring.

Example 12

Preparation of ACP:HBC 500 Gel, in the Ratio of 25:75

Process B 6.25 g of internal ester of hyaluronic acid ACP 200 is solubilised in 250 ml of a solution containing 4.4 g of NaCl under slow stirring. When hydration has been completed, the gel is combined with the gel obtained according to example 11 in a mixer equipped with a system for mixing semisolids, until homogenous. The gel obtained is extruded through a flat membrane filter with a nominal particulate matter retention rate of 70 µm. The product thus obtained is introduced into glass syringes and sterilised in a cycle with F0=13 at 121.5° C.

Example 13

Preparation of HYADD:HBC 500 Gel, in the Ratio of 25:75

Process B 6.25 g of HYADD hexadecylamide is solubilised in 250 ml of a solution containing 4.4 g of NaCl under slow stirring. When hydration has been completed, the gel is combined with the gel obtained according to example 11 in a mixer equipped with an orbital mixing system, until homogenous. The gel obtained is extruded through a flat membrane filter with a nominal particulate matter retention rate of 70 µm. The product thus obtained is introduced into glass syringes and sterilised in a cycle with F0=13 at 121.5° C.

Example 14

Synthesis of HBC 500 (HA 500-730 kDa)

Process B 125 g of HA sodium salt with a molecular weight of 500-730 kDa, produced by fermentation, is dispersed in 1.33 µl of an 0.25M NaOH solution containing 9.4 ml of BDDE. The mixture is heated at 45° C. for 2.5 hours. The mixture is hydrated overnight with 6.2 l of a solution containing a stoichiometric amount of HCl, 26.5 g of NaCl and 27 g of lidocaine hydrochloride, under slow stirring.

Example 15

Preparation of ACP:HBC 500 Gel, in the Ratio of 50:50

Process B 125 g of internal ester of hyaluronic acid ACP200 is solubilised in 2.5 l of a solution containing 44 g of NaCl under slow stirring. When hydration has been completed, the gel is combined with the gel obtained according to example 14 in a mixer equipped with an orbital mixing system with buffle and scraper. The gel obtained is extruded through a flat membrane filter with a nominal particulate matter retention rate of 45 µm. The product thus obtained is introduced into glass syringes and sterilised in a cycle with F0=13 at 121.5° C.

Example 16

Cutaneous Filling and Tolerability of ACP:HBC Gel in the Intradermal Rabbit Administration Model The experiment was performed as described in example 10, using gel prepared as described in examples 11-12, and comparing it with the Belotero® control and with a second commercial filler, Regenyal Idea.

For this experiment, the Applicant not only determined the skin swelling volume caused by the treatment but also evaluated the total residence time of the gel/filler according to the invention by comparison with two well-known commercial fillers which represent the final comparator because both consist of HA crosslinked with BDDE.

The skin swelling in the treated rabbits was measured fortnightly (with macroscopic observation for adverse events) for a maximum of 96 days.

Figure 2:
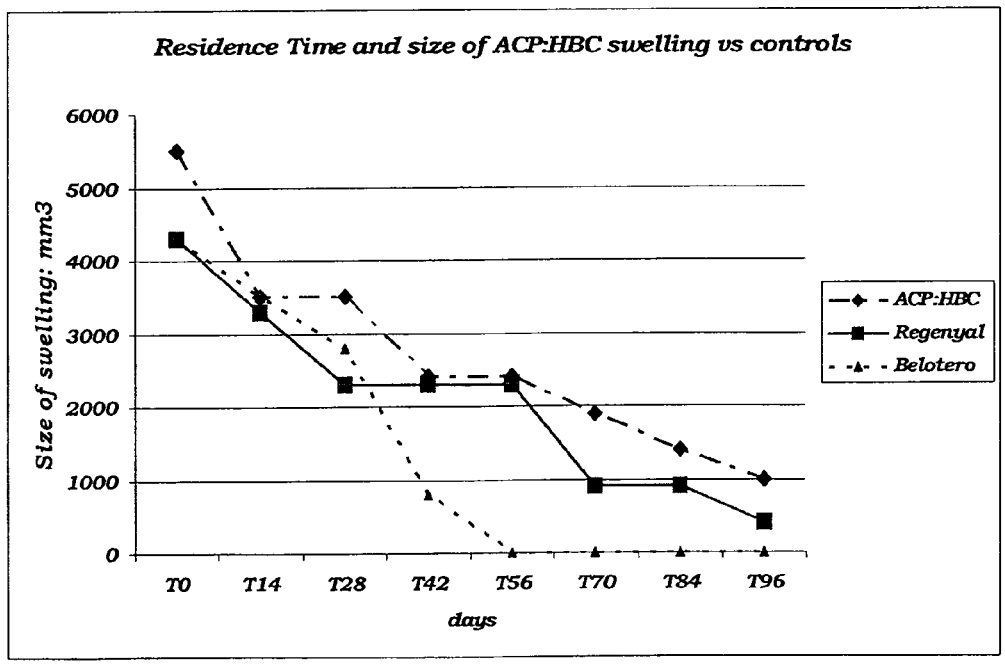
FIG. 2 graphs the results of a test on the cutaneous filling and tolerability of ACP:HBC gel in the intradermal rabbit administration model.

Results:

FIG. 2 shows the results obtained: the findings described above were confirmed, namely immediate hydration of the treated dermis (mainly within the first 7 days) to a surprisingly greater extent than in the controls; moreover, the size of the skin swelling was more evident and the residence time longer than those of the two commercial comparators. At the end of the experiment, the novel filler according to the invention was still present, whereas the two controls had almost disappeared.

The methods described herein can clearly be modified in various ways. Such modifications should not be considered to depart from the spirit and prospects of the invention, and all modifications which would appear evident to a skilled person are included in the scope of the following claims.

The invention claimed is:

1. A biomaterial for use as a filler and/or as a body shaping product prepared by a process comprising:
   (a1) mixing an autocrosslinked hyaluronic acid (ACP) powder with (HBC) a hyaluronic acid crosslinked with 1,4-butanediol diglycidyl ether (HBC) in a weight ratio of between 10:90 and 90:10, wherein the hyaluronic acid in said ACP and HBC has a mean molecular weight of between 200,000 and 1×10$^6$ Da;
   (b1) hydrating with saline solution or phosphate buffer, leading to a total hyaluronic acid concentration of between 12 and 27 mg/ml;
   (c1) extruding at a temperature of between 25 and 65° C. through a sieve with a mesh of between 50 and 500 □m; and
   (d1) sterilizing by heat from saturated steam at a temperature of between 120 and 124° C. for at least 10 min; or
   (a2) mixing an autocrosslinked hyaluronic acid (ACP) gel or powder with a hyaluronic acid crosslinked with 1,4-butanediol diglycidyl ether (HBC) in gel form in a weight ratio of between 10:90 and 90:10;
   (b2) crushing and homogenizing by passing through a filter with a particulate matter retention coefficient of between 25 and 150 µm; and
   (c2) sterilizing by heat from saturated steam at a temperature of between 120 and 124° C. for at least 10 min.

2. A biomaterial for use as a filler and/or as a body shaping product prepared by a process comprising:
   (a1) mixing a hyaluronic acid hexadecylamide (HYADD) powder with a hyaluronic acid crosslinked with 1,4-butanediol diglycidyl ether (HBC) in a weight ratio of between 10:90 and 90:10;
   (b1) hydrating with saline solution or phosphate buffer, leading to a total hyaluronic acid concentration of between 12 and 27 mg/ml;
   (c1) extruding at a temperature of between 25 and 65° C. through a sieve with a mesh of between 50 and 500 µm; and
   (d1) sterilizing by heat from saturated steam at a temperature of between 120 and 124° C. for at least 10 min; or
   (a2) mixing a hexadecylamide (HYADD) gel or powder with a hyaluronic acid crosslinked with 1,4-butanediol diglycidyl ether (HBC) in gel form in a weight ratio of between 10:90 and 90:10;
   (b2) crushing and homogenizing by passing through a filter with a particulate matter retention coefficient of between 25 and 150 µm; and
   (c2) sterilizing by heat from saturated steam at a temperature of between 120 and 124° C. for at least 10 min.

3. The biomaterial as claimed in claim 1 or 2, wherein the weight ratio is 90:10 to 50:50.

4. The biomaterial as claimed in claim 1 or 2, wherein the weight ratio is 10:90 to 50:50 with a volume-enhancing effect.

5. The biomaterial as claimed in claim 4, wherein the weight ratio is 25:75.

6. A process of mixing an autocrosslinked hyaluronic acid (ACP) or a hyaluronic acid hexadecylamide (HYADD) with a hyaluronic acid crosslinked with 1,4-butanediol diglycidyl ether (HBC), comprising the following steps:
   (a) mixing ACP or HYADD with HBC in a ratio of ACP:HBC or HYADD:HBC of between 90:10 and 10:90;
   (b) hydrating with saline solution or phosphate buffer, leading to a total hyaluronic acid concentration of between 12 and 27 mg/ml;
   (c) extruding at a temperature of between 25 and 65° C. through a sieve with a mesh of between 50 and 500 µm;
   (d) syringe filling; and
   (e) sterilizing by heat from saturated steam at a temperature of between 120 and 124° C. for at least 10 min.

7. A process of mixing an autocrosslinked hyaluronic acid (ACP) or a hyaluronic acid hexadecylamide (HYADD) with a hyaluronic acid crosslinked with 1,4-butanediol diglycidyl ether (HBC), comprising the following steps:
   (a) mixing ACP or HYADD with HBC in a ratio of ACP:HBC or HYADD:HBC of between 90:10 and 10:90;
   (b) crushing and homogenizing by passing through a filter with a particulate matter retention coefficient of between 25 and 150 µm;

(c) syringe filling; and (d) heat sterilisation with saturated steam at a temperature of between 120 and 124° C. for at least 10 min.

8. The process as claimed in claim 6 or 7, wherein a hyaluronic acid used for the preparation of the HBC, ACP and HYADD has a mean molecular weight of between 400 and $3 \times 10^6$ Da.

9. The biomaterial as claimed in claim 1, 4 or 5, wherein the ACP:HBC weight ratio is 25:75.

10. The biomaterial as claimed in claim 1 or 2, comprising saline solution as a vehicle.

11. The biomaterial as claimed in claim 1 or 2, containing lidocaine.

12. The biomaterial as claimed in claim 9, containing lidocaine and saline solution as a vehicle.

13. The biomaterial according to claim 1, wherein said ACP has a mean degree of cross-linking of between 4 and 5%.

14. The biomaterial according to claim 13, wherein the hyaluronic acid in said ACP has a mean molecular weight of about 200,000 Da.

15. The biomaterial according to claim 2, wherein said HYADD has a mean degree of amidation/substitution of between 1 and 3% in moles.

16. The biomaterial according to claim 15, wherein the hyaluronic acid in said HYADD has a molecular weight of between 500,000 to 730,000 Da.

\* \* \* \* \*